United States Patent [19]
Flewitt

[11] Patent Number: 6,161,260
[45] Date of Patent: Dec. 19, 2000

[54] PHARMACEUTICAL TABLET DESIGNED FOR EASIER BREAKING

[76] Inventor: Harry Flewitt, SmithKline Beecham Corporation Corporate Intellectual Property - UW2220 P.O. Box 1539, King of Prussia, Pa. 19406-0939

[21] Appl. No.: 09/308,864
[22] PCT Filed: Nov. 24, 1997
[86] PCT No.: PCT/EP97/07000
§ 371 Date: May 26, 1999
§ 102(e) Date: May 26, 1999
[87] PCT Pub. No.: WO98/23264
PCT Pub. Date: Jun. 4, 1998
[51] Int. Cl.[7] .............................................. A61K 9/20
[52] U.S. Cl. ..................... D24/101; D24/103; 424/464; 424/465
[58] Field of Search .................................. D24/101, 103

[56] References Cited

U.S. PATENT DOCUMENTS

| | | | |
|---|---|---|---|
| D. 228,456 | 9/1973 | Ninger | D16/3 |
| D. 316,616 | 4/1991 | Leslie et al. | D28/2 |
| D. 398,395 | 9/1998 | Titley et al. | D24/101 |
| 3,336,200 | 8/1967 | Krause et al. | |
| 4,258,027 | 3/1981 | Ullman et al. | |
| 4,824,677 | 4/1989 | Shah et al. | |

FOREIGN PATENT DOCUMENTS

| | | |
|---|---|---|
| 0 531 964 | 3/1993 | European Pat. Off. . |
| 2462908 A1 | 2/1981 | France . |
| 683066 A5 | 1/1994 | Switzerland . |

Primary Examiner—Thurman K. Page
Assistant Examiner—Amy E. Pulliam
Attorney, Agent, or Firm—Nora Stein-Fernandez; Janice E. Williams; Stephen Venetianer

[57] ABSTRACT

A pharmaceutical tablet, with a break line aligned along a long dimension of the tablet, such that a twisting action, in which parts of the tablets on opposite sides if the break line are subjected to a rotational twisting force in respectively opposite senses, causes the tablet to break into two or more parts. The tablet is of the type which may be broken into two or more parts in order to ease swallowing or to allow administration of a partial dose.

30 Claims, 6 Drawing Sheets

PHARMACEUTICAL TABLET DESIGNED FOR EASIER BREAKING

This invention relates to pharmaceutical tablets of the type which may be broken into two or more parts to ease swallowing or to allow administration of a part dose.

Pharmaceutical tablets are often made having a break line, usually a groove, aligned perpendicular to major dimension of the shape, e.g. the length or width, so that the tablet can be easily broken in-two by a folding snapping action. A problem with such tablets is that some patients can find them difficult to break, particularly if they have weak or deformed hands, such as arthritis sufferers. Typically if a small tablet of this type is broken by a folding action the user's thumbs and/or fingers are forced uncomfortably together as the tablet folds.

Various tablet shapes are known which have features which are alleged to improve the ability of a user to break the tablet into two or more parts. For example U.S. Pat. No. 4,258,027 discloses tablets provided with at least two break lines. EP 0658104 A discloses an elongated tablet with bulges at each end and a break line across the longitudinal middle, which are alleged to be easily broken by pressing onto a surface. EP 0531964 A also discloses tablets in the form of two lobes with a break line diametrically across the long dimension of the tablet between the lobes. U.S. Pat. No. 4,824,677 discloses an elongate tablet with a mid-longitudinal break line. Design registrations and design patents also disclose twin lobed tablets with a mid-longitudinal break line, e.g. U.S. Pat. No. Des. 228,456, U.S. Pat. No. Des. 229,275, and ZA Des 92/634.

It is an object of this invention to provide a novel tablet construction in which this problem is at least partly alleviated.

According to this invention, a pharmaceutical tablet has a break line aligned across a long dimension of the tablet such that a twisting action, in which parts of the tablets on opposite sides of the break line are subjected to rotational twisting force in respectively opposite senses, causes the tablet to break along a line substantially following the break line, into two or more parts.

The provision by the invention of a tablet which is broken by a twisting rather than a folding action solves the above-mentioned problem in that the use of a twisting action to apply the above-mentioned twisting force does not cause the thumbs and/or fingers of the user to come together during the breaking of the tablet.

In one embodiment of the invention, the tablet is of a shape flattened about a plane, having a length and width dimension in the plane into which the tablet is flattened, and with a thickness dimension perpendicular to this plane and less than either the length or width, the length and width thereby being both "long dimensions" relative to the shorter thickness dimension, and the break line may follow a generally straight line or a curve, such as a gentle "S", "Z" or sinusoidal curve, across the length or width of the tablet, preferably across the width.

The tablet of the invention has upper and lower surfaces distanced by a thickness dimension, and side surfaces between the said upper and lower surfaces.

The length and width may be substantially the same, such that the tablet is of generally circular, square or polygonal (optionally with rounded ends or corners) shape in plan.

In another, preferred, aspect of this invention, a pharmaceutical tablet has an elongated shape flattened about a plane, having a major ("length") dimension and a minor ("width") dimension in the plane into which the tablet is flattened, and a thickness dimension perpendicular to this plane and less than either the length or width, and the tablet has a break line across the major dimension and aligned diagonally, i.e. at an angle other than 90°, relative to the major dimension.

In such a tablet a twisting action, in which parts of the tablets on longitudinally opposite sides of the break line are subjected to rotational force in respectively opposite senses about the major dimension as rotation axis, causes the tablet to break, along a line substantially following the break line, into two or more parts.

Suitable elongated shapes are those which in plan view, i.e the view perpendicular to the length and width dimensions are oval, elliptical, lozenge or capsule-shaped (i.e. rectangular with rounded ends), pillow shaped or rectangular with rounded corners, diamond or parallelogram shaped with rounded corners, almond shaped, arrow head shaped, bullet shaped and half moon shaped.

In another particularly preferred aspect of this invention the tablet has an elongated shapes which in plan has two lobes on either longitudinally disposed side of the longitudinal mid-point of the tablet, e.g. at the longitudinally disposed ends of the tablet, with a waist which is narrower in width than the widest part of each lobe, longitudinally in between the lobes, e.g. at or near the longitudinal mid point of the tablet. Such a waist can serve to create a line of weakness across the width of the tablet, to direct and concentrate the twisting force and can assist the tablet to easily break across its width.

The shape of each of the two lobes of the tablet may be symmetrical about the longitudinal axis. In a preferred embodiment the shape of each of the two lobes of the tablet is un-symmetrical about the longitudinal axis. Such asymmetry can assist the user in gripping the tablet by the longitudinally distanced lobes and to apply twist forces thereto about the longitudinal axis. For example each lobe may bulge more prominently widthways, e.g. to a greater distance or area on one widthways side of the longitudinal axis than the other. For example each lobe may be differently shaped on one widthways side of the longitudinal axis than the other. For example where the side surfaces of the lobes converge toward the narrowed waist of the tablet, the parts of the side surfaces of each lobe on respective opposite sides of the longitudinal axis may converge at different angles towards the longitudinal axis, i.e. the convergence toward the longitudinal axis may be steeper on one side than the other.

Examples of such two-lobed shapes are tablets which in plan are "peanut"-shaped; dumb-bell shaped; figure of eight-shaped; of a shape with two circular or oval shaped lobes; of a shape with polygonal lobes which may have rounded corners, a corner or edge of each such polygonal lobe overlapping with a corner or edge of the other lobe, of which the circumference, perimeter, edge or corners of each of such lobes overlaps with the circumference, perimeter, edge or corners of the other lobe, or instead of overlapping the circumference, perimeter, edge or corners of the lobes may be longitudinally distanced or may contact tangentially without any overlap.

Some examples of such shapes are described below.

One example of such a shape in plan comprises two generally circular lobes of radius R, and in which the extrapolated arcs of the circles either meet with no overlap, or which overlap, for example to a distance of about 0.25–0.75 R typically around 0.3–0.6 R. The term "generally circular" in this context includes inter alia oblate circular, semicircular and shapes in which a substantial part of the perimeter, e.g. 50% or more, e.g. 75% or more is circular, e.g distorted circles but having an overall rounded perimeter. Alternatively such lobes may be generally oval and their extrapolated arcs can either meet with no overlap, or may overlap, e.g for up to 50% of the area of each oval. The term "generally oval" in this context includes inter alia elliptical, semi-elliptical, semi-oval and shapes in which a substantial part of the perimeter, e.g. 50% or more, e.g. 75% or more, is oval.

By "extrapolated" as used herein is meant that the perimeter of the lobes on either longitudinal side of the region where they join describes generally a shape bounded by a perimeter, and the perimeter may be theoretically continued across the region where they join, e.g. across the waist of the tablet.

On either widthways side of such two-lobed tablets, e.g. about the regions where the extrapolated arcs of the circles or ovals meet or cross, a concave indent will be formed which can be shaped into a smooth concave indented curve, and the waist of the tablet extends between these indents. This concave indent may be made asymmetrical about an axis linking the most deeply indented parts of the indents, and this can cause the one of the lobes to bulge more prominently on one side of the longitudinal axis than the other lobe. For example this may be achieved by part of the perimeter of the lobe immediately adjacent to the indent being aligned more steeply toward the longitudinal axis than the corresponding part of the perimeter on the longitudinally opposite side of the indent. This may assist the user in applying twisting force to break the tablet.

The respective geometric centres of each of such lobes, e.g. the centres of generally circular lobes, or the mid point between foci of generally oval lobes, may be displaced to respective opposite sides of the long dimension, in the plane in which the tablet shape is flattened. In the case of generally circular or generally oval lobes, the centres may be so displaced typically to 0.05–0.3 of radius R, typically to a distance of about 0.1–0.2 of radius R on each widthways side of the long dimension. This causes the lobes to bulge out to different distances on the respective sides of the long dimension as above-mentioned. This may assist the user in applying twisting force about the axis of the long dimension to break the tablet.

Another example of such a shape in plan comprises two generally quadrilateral, e.g. generally square, rectangular or diamond shaped lobes, which may have rounded, even substantially rounded, corners or ends, for example being substantially lozenge shaped, and an extrapolated corner or side of each such lobe may overlap with a corner or side of the other lobe, typically with up to ca. 50%, for example between ca. 15%–40%, e.g. ca. 20%–30% of the respective areas of the lobes as viewed perpendicular to the plane in which they are flattened, i.e down the thickness direction, overlapping. Instead of overlapping the perimeter of the lobes may be longitudinally distanced or may contact tangentially without any overlap. When generally rectangular lobes overlap in the above-described manner, the area of overlap may itself be rectangular, so that for example the respective long sides of the rectangle overlap for 30% or more, preferably 50% or more, and likewise the respective short sides of the rectangle overlap for 30% or more, preferably 50% or more of their length.

The sides of such quadrilateral lobes, e.g. the long sides of rectangular lobes, may be aligned generally parallel with the length direction of the tablet, or alternatively may be aligned at an angle to the length dimension. About the points where the respective perimeters of the two lobes meet a concave indent will be formed, which can be shaped into a smooth concave indented curve. When the lobes are generally rectangular, they may have ratios of long side:shorter side of ca. 2:1–1.2:1, typically around 1.5:1–1.7:1.

As abovementioned, the shape of each of the two generally quadrilateral lobes of the tablet may be symmetrical about the longitudinal axis, but in a preferred embodiment the shape of each of the two generally quadrilateral lobes of the tablet is un-symmetrical about the longitudinal axis. For example each lobe may bulge more prominently widthways, e.g. to a greater distance or area on one widthways side of the longitudinal axis than the other. For example each lobe may be differently shaped on one widthways side of the longitudinal axis than the other. For example where the side surfaces of the lobes converge toward the narrowed waist of the tablet, the parts of the side surfaces of each lobe on respective opposite sides of the longitudinal axis may converge at different angles towards the longitudinal axis, i.e. the convergence toward the longitudinal axis may be steeper on one side than the other.

Another example of such a shape is one in which the two lobes are each in plan view of a shape which is substantially circular or oval (as defined above) over 50% or more, e.g 60% or more of their perimeter, the remainder of the perimeter of each lobe being a substantially straight line along the line of a chord or part of a chord of the said substantially circular or oval part of the perimeter, the two lobes meeting and facing each other along the line of the chords, the chords being aligned transverse to the longitudinal axis of the tablet, the geometric centres of the lobes being respectively displaced relative to each other in a direction parallel to the line of the chords in respective opposite directions on either widthways side of a line perpendicular to the line of the chords. The displacement may be to the same distance on respective opposite sides of the said line.

For example in the case of substantially circular lobes of radius R the lobes may be respectively displaced by 0.1–0.8 R relative to each other in a direction parallel to the line of the chords in respective opposite directions on either widthways side of a line perpendicular to the line of the chords.

Suitably the tablet shape has upper and lower surfaces distanced by the thickness dimension. These upper and lower surfaces may be flat, or may be convex in shape, e.g. domed in shape or have low pyramidal or polyhedral shapes, which shapes may be either symmetrical or asymmetrical relative to mirror planes parallel to the length or width dimension, e.g. to facilitate grip, to facilitate twisting, to give an aesthetic appearance, to enable the tablet to stand proud of a surface on which is placed as so to facilitate picking up from the surface etc. For example if the tablet is of a shape having two lobes, as described above, the two lobes may be asymmetrical in this way about a mirror plane aligned parallel to the length dimension. For example the upper and lower surfaces may bulge in the thickness direction asymmetrically about a mirror plane parallel to the length dimension, for example bulging in the thickness direction more on one widthways side of the length dimension than on the other. Such asymmetry can also assist the user to grasp the tablet by the lobes and to apply an opposite twisting force to each respective lobe.

The tablet shape has side surfaces which may be substantially parallel to the thickness dimension all around the tablet perimeter, or curved, or profiled in other ways. The side surfaces may meet the upper and lower surfaces by a distinct edge, e.g. a chamfered edge or in a smooth curve with no distinct edge. Typically the thickness of such a tablet may be 1–1.5 R at the geometric centres of generally circular lobes, or 0.2–0.75, e.g. ca. 0.5±0.1 of the long side dimension of generally rectangular lobes at the geometric centres of generally rectangular lobes.

The break line preferably runs diagonally across the width of an elongate shape tablet, that is, generally crossing the major dimension at an angle "α" other than 90°. For example the break line may cross the major dimension at an acute angle of 30°–80°, e.g. 45°–80°, e.g. 60°–80°, such as 60°–75°. It is understood that although, in some embodiments of the invention at the actual point where the break line intersects the longitudinal axis the intersection may be at 90°, the overall alignment of the whole break line may be other than 90°, for example by virtue of the break line following an "S" curved path across the tablet, such that only the central part of the S is aligned at 90° to the longitudinal axis and a theoretical line joining the two ends of the break line may be aligned at other than 90° to the longitudinal axis. When the tablet shape is an elongated shape having two lobes at the longitudinally disposed ends of the tablet with a narrower waist in between, as described above, the break line may run between the concave indents, for example running between their most indented parts, where the perimeters of the two lobes intersect and crossing the waist of the tablet.

The break line may be formed by virtue of the inherent weakness of the tablet at the narrow waist between the two lobes, thereby providing a tendency for the tablet to break along a line generally following the waist. When the tablet shape is an elongated shape having two lobes at the longitudinally disposed ends of the tablet with a narrower waist in between, e.g. at or near the longitudinal mid point, as described above, normally there will be two concave indents at opposite widthways separated positions on widthways opposite sides of the longitudinal axis, where the two lobes meet, for example where the circumference of circular lobes or the edges of polygonal lobes intersect, and an inherent line of weakness occurs between the two concave indents where the perimeters of the lobes meet, without the need for a groove in the tablet surface.

Additionally or alternatively if the tablet is of a shape having two longitudinally separated lobes as described above, if these lobes have domed, pyramidal or polyhedral upper and lower surfaces, then the thickness of the tablet at the lobes may be greater than in the region of the tablet between the lobes, thereby forming a "valley" or "saddle" between them. A line of weakness along the line of such a valley, e.g. across the width of the tablet between the lobes, can result from such a valley. These features can provide a tendency for the tablet to break along these lines of weakness without any need for an additional groove.

A break line may additionally or alternatively be provided or accentuated in the form of a distinct groove in the tablet surface as commonly used in the breakable tablet art.

Such a groove may run only across the width of the tablet. In such a case the groove may run across one or both of the upper and lower tablet surfaces. Alternatively the groove may run all around the tablet, i.e. over the upper and lower surfaces and up and down the side surfaces which join them. The deepest parts of the above-described concave indents may additionally comprise a break line on the side surfaces of the tablet.

The break line may suitably be in plan a generally straight line, e.g. having its bottom, and suitably also its upper edges a substantially straight line, for example a groove having this profile. Alternatively the break line may be formed by or be accentuated by a groove having upper edges where the sides of the groove meet the upper and lower surfaces, and having a bottom, wherein the bottom follows substantially a straight line and the upper edges of the groove may follow a curve. Alternatively the break line may be formed by or be accentuated by a groove the bottom of which and the edges of which in plan follow a curve, such as a gentle "S", "Z" or sinusoidal curve. The shape of the break line in plan may for example be curved such that the formation of sharp points is reduced or avoided when the tablet breaks. For example the break line may cross most of the width of the tablet diagonally in for example a generally straight line or a gentle curve, but the parts of the break line immediately adjacent to the sides of the tablet may bend to meet the edges perpendicularly or at a steep angle to avoid formation of a point, which might result in the formation of sharp points on the broken parts of the tablet after it is broken.

Such a groove may be generally "V" shaped in cross section or may have other profiles known in the tablet art. A break line groove of generally "V" shaped cross section may have an angle between the limbs of the "V" of typically between 60°–120°, typically around 90°, e.g. 80°–100°. Suitably at its deepest, the depth of the break line groove may be 0.1–0.3, preferably 0.125–0.25 of the thickness of the region of the tablet crossed by the break line. Suitable profiles of groove for any particular application can easily be determined by those skilled in the art.

Additionally or alternatively the break line may be formed or accentuated by other ways used in the tablet art of reducing the thickness of the tablet along a line across which the tablet is preferentially desired to break, or other types of lines of weakness across the tablet.

Preferably the tablet of the invention is constructed such that it breaks into two parts. Preferably these two parts are two substantially equally sized parts, each of such parts including a half-dose or a single unit dose of the active medicament content which may be taken separately.

The tablet of the invention can be broken by the above-described twisting action in which the user holds parts of the tablet disposed on longitudinally opposite sides of the longitudinal mid point and applies twist forces of opposite twist senses to thereby break the tablet in two. The tablet can also be broken by a conventional folding snapping action, in which a folding action is applied to the tablet about the widthways axis as a fold axis.

The tablet of the invention may also incorporate the feature of EP 0055009A, the content of which is included by reference, so that its shape is such that its most stable position on a horizontal flat surface is a tilted position. For example this feature may be imparted to the tablet of the invention by making it of a shape in which there is an inbuilt twist about the major dimension, such that respective parts of the tablet on longitudinally opposite sides of the break line are each flattened about a respective plane parallel to the major dimension and to the width of the part, and these respective planes are each rotated about the axis of the major dimension at an angle relative to each other. To retain a generally flattened overall tablet shape this angle may be a small angle. A suitable small angle is ca. 5°–30°. This feature can render the tablet more easy for patients with weak or deformed hands to pick up from a surface such as a table.

The tablets of the invention may be formulated and made by known processes suitable to the substances, e.g. pharmaceutical compound and excipients they contain, and may be of a size and weight comparable to conventional tablets.

Suitably the tablet of the invention may contain a number of unit doses of a pharmaceutical compound(s) corresponding to the number of parts the tablet is intended to break into, for example when the tablet comprises two lobes as described above each such lobe may contain half a single unit dose, or may contain a single unit dose for taking twice per day. Suitable dimensions for the overall tablet and its break line can easily be determined by experiment.

The tablet of the invention is suitable for use with all known types of orally administered drugs. The tablet of the invention is particularly suitable for use with such drugs as are used in small quantities so that the tablet is of a small overall size, e.g. less than ca. 1 cm in longest dimension, although it is also suitable for larger tablets. The tablet of the invention is also particularly suitable for use with drugs which are intended or suitable for administration to patients with weak or deformed hands.

The invention will now be described by way of example only with reference to the following drawings.

Figures 1, 2:
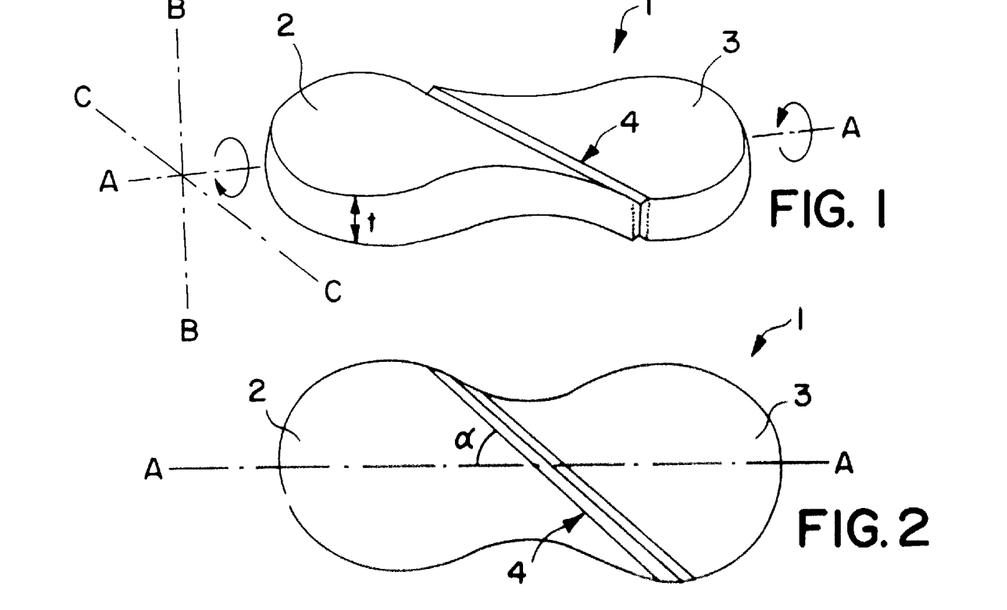
FIG. 1 shows a perspective view of a tablet of this invention
FIG. 2 shows a plan view of the tablet of FIG. 1.
Figure 3:
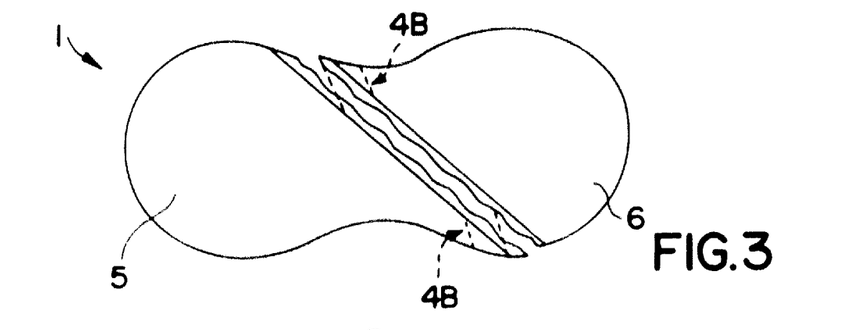
FIG. 3 shows a plan view of the tablet of FIG. 1 when broken

Referring to FIGS. 1, 2 and 3, a tablet is shown 1 overall, which is of a shape elongated along a major dimension A—A, being the longitudinal axis, i.e. the length dimension. In plan, looking down the thickness dimension B—B the shape has two rounded lobes 2, 3 on either longitudinally disposed side of the longitudinal mid-point of the tablet, i.e. at its longitudinally disposed ends, i.e. the tablet 1 being generally a peanut or dumbbell shape in plan. In elevation as seen along the width dimension C—C the thickness t of the tablet 1 is much less than the width, i.e. the dimension of the tablet 1 in the direction C—C, so that the overall shape is flattened in the thickness direction about a plane, being the plane of the paper in FIGS. 2 and 3 in which the major dimension A—A and the dimension C—C lie.

A break line is formed by a V-sectioned groove 4 which runs all around the tablet 1, i.e. across the width C—C and up the thickness B—B of its side surfaces. The groove 4 crosses the major dimension A—A diagonally, i.e. forming an angle α less than 90° with the major dimension A—A.

If the tablet of FIGS. 1 to 3 is twisted about the axis of its major dimension A—A, so that the lobes 2, 3 are subjected to rotational forces in respectively opposite senses about the axis of its major dimension A—A, i.e. as shown by the in FIG. 1, the tablet breaks about the break line 4 into two substantially equally sized halves 5, 6, as shown in FIG. 3. If this is performed by the patient gripping each lobe 2, 3 in a different hand and twisting, the tablet 1 is broken without the user's thumbs and/or fingers being brought together. As shown in FIG. 3 the broken halves 5, 6 of the tablet have sharp points at 4A, and these may be avoided by curving the break line as shown by the dotted line 4B, such that the break line 4 meets the side surfaces of the tablet at approximately 90°.

Figure 4:
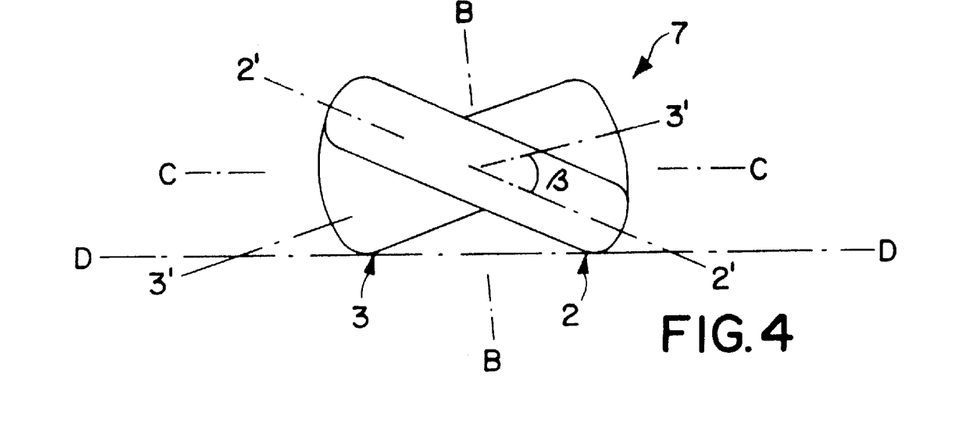
FIG. 4 shows a longitudinal end view of a tablet of this invention having an inbuilt twist.

Referring to FIG. 4, a view along the major dimension A—A of a tablet 7 is shown. In plan and overall shape the tablet 7 is similar to the tablet 1, but each of the lobes 2, 3 is flattened about a respective plane 2'—2', 3'—3' which is parallel to the major dimension A—A and to the width of the part, and these planes are rotated about the major dimension A—A relative to each other by a small angle β, about 20°. This means that when the tablet is laid on a flat surface aligned on the line D—D such as a table, the edges of the lobes 2, 3 rest on the surface, and its shape is such that its most stable position is a position in which each lobe of the tablet is tilted relative to the surface, e.g. at an angle β/2 and is thus easy to pick up. The tablet 7 is provided with a break line similar to 4 of FIGS. 1–3 and is broken by twisting in a similar manner.

Figure 5A:
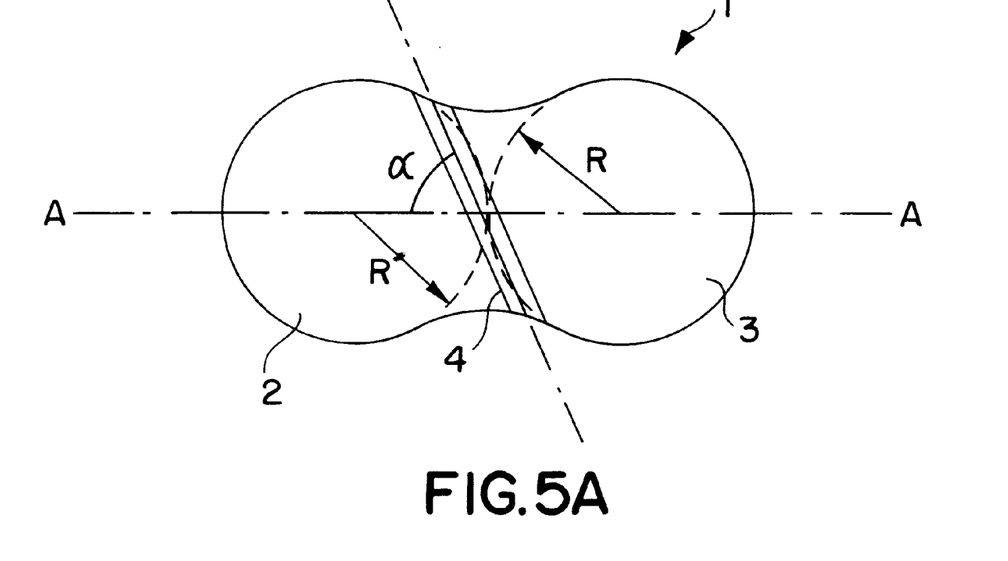
FIG. 5 shows a plan view and longitudinal section of a further tablet of this invention.
Figure 5B:
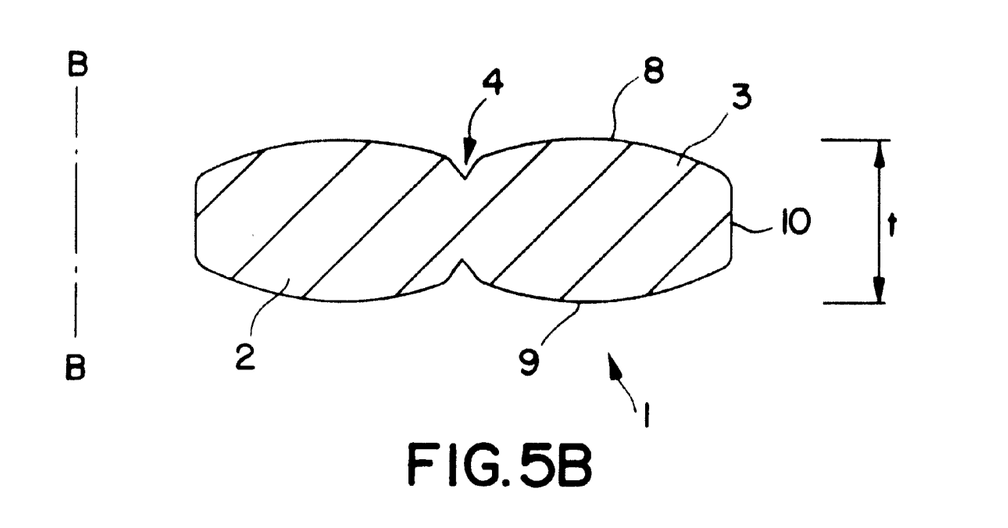

Referring to FIG. 5 parts in common with FIG. 1 are numbered correspondingly. In FIG. 5 the lobes 2, 3 are of generally circular shape, each lobe having the same radius R about centres located on the longitudinal dimension A—A. As shown by dotted lines in FIG. 5 the extrapolated arcs of these two circles meet without overlap at the longitudinal mid point. The break line 4 is a "V" sectioned groove extending only across the upper 8 and lower 9 surfaces of the tablet, which are domed as shown in the longitudinal section. As seen in the longitudinal section FIG. 5, longitudinally between these domed upper and lower surfaces 8, 9 of the lobes is a valley running across the width of the tablet. The break line 4 has a bottom which extends in a substantially straight line diagonally across the length dimension, and forming an angle α of about 60° with the length dimension, the upper edges 4C of the break line 4 also lying in a substantially straight line. Around the tablet is a side surface 10, with surfaces substantially parallel to the thickness "t" dimension B—B which meets the domed upper-and lower surfaces with rounded edges. About the points where the respective perimeters of the two lobes 2, 3 meet concave indents 11 are formed, which are shaped into a smooth concave indented curve.

Figure 6A:
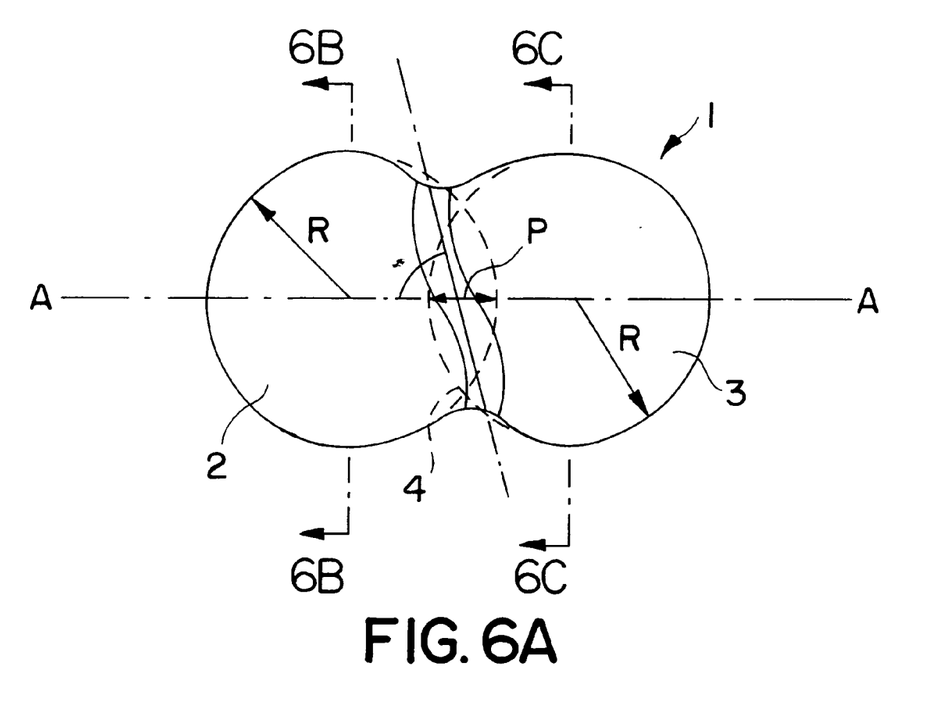
FIG. 6 shows a plan view and cross sections of a further tablet of this invention.
Figure 6B:
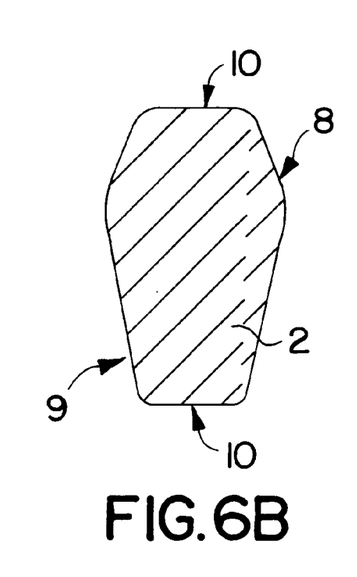
Figure 6C:
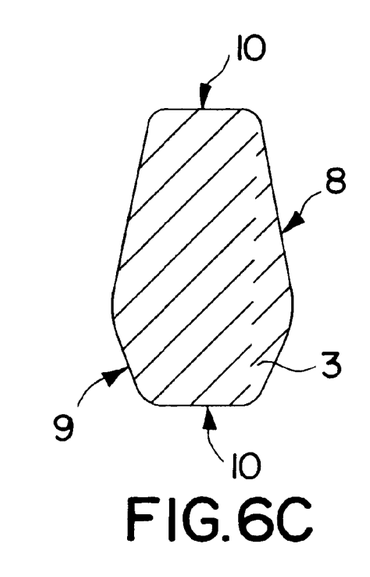

Referring to FIG. 6 parts in common with FIG. 1 are numbered correspondingly. In FIG. 6 the lobes 2, 3 are of generally circular shape, each lobe having the same radius R about centres located on the longitudinal dimension A—A. As shown by dotted lines in FIG. 5 the arcs of these two circles overlap for a distance "P" which is about 0.4 of radius R at the longitudinal mid point. The break line 4 is a "V" sectioned groove extending only across the upper 8 and lower 9 surfaces of the tablet, with a valley in between. The longitudinal section of the tablet of FIG. 6 is similar to that of the tablet of FIG. 5. As shown in the cross sections about the lines X—X and Y—Y the upper and lower surfaces 8, 9 are domed asymmetrically about the width dimension, bulging in the thickness direction B—B more on one widthways side of the length dimension A—A than on the other. The break line 4 has a bottom which extends in a substantially straight line diagonally across the length dimension, and forming an angle α of about 75° with the length dimension, but the upper edges of the break line follow a gentle curve, substantially along the straight line of the bottom of the groove. Around the tablet is a side surface 10, with surfaces substantially parallel to the thickness dimension B—B. About the points where the respective perimeters of the two lobes 2, 3 meet concave indents 11 are formed, which are shaped into a smooth concave indented curve.

Figure 7:
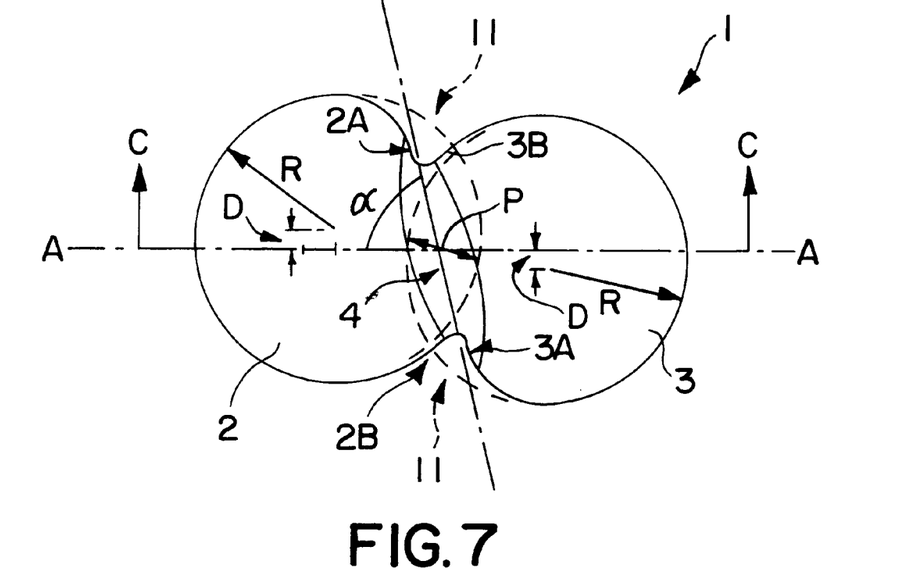
FIG. 7 shows a plan view of a further tablet of this invention.

Referring to FIG. 7 parts in common with FIG. 1 are numbered correspondingly. In FIG. 7 the lobes 2, 3 are of generally circular shape, each lobe having the same radius R, the respective centres of these generally circular lobes 2, 3, being displaced to opposite sides of the long dimension A—A, each respectively to a distance "D" of about 0.1 of radius R on each side. This causes the lobes to bulge out to different distances in the width direction on the respective sides of the long dimension. As shown by dotted lines in FIG. 7 the arcs of these two circles overlap for a distance "P" which is about 0.4 of radius R at the longitudinal mid point. The break line 4 is a "V" sectioned groove extending across the upper 8 and lower 9 surfaces of the tablet, which are domed, the longitudinal section about line C—C being similar to that shown in FIG. 5. The break line 4 has a bottom which extends in a substantially straight line diagonally across the length dimension A—A, and forming an angle α of about 75° with the length dimension A—A, but the upper edges of the break line follow a gentle curve, substantially following the straight line of the bottom of the groove. Around the tablet is a side 10, (not shown in FIG. 7) with surfaces substantially parallel to the thickness dimension B—B. About the points where the respective perimeters of the two lobes 2, 3 meet deep concave indents 11 are formed, which are shaped into a smooth concave indented curve. The concave indents 11 are asymmetrical about an axis linking the most deeply indented parts of the indents 11, part of the perimeter 2A, 3A immediately adjacent to the indent being aligned more steeply toward the longitudinal axis than the corresponding part of the perimeter 2B, 3B on the longitudinally opposite side of the indent. This causes one of the lobes 2, 3 to bulge more prominently on one side of the longitudinal axis A—A than the other lobe 2, 3.

Figure 8:
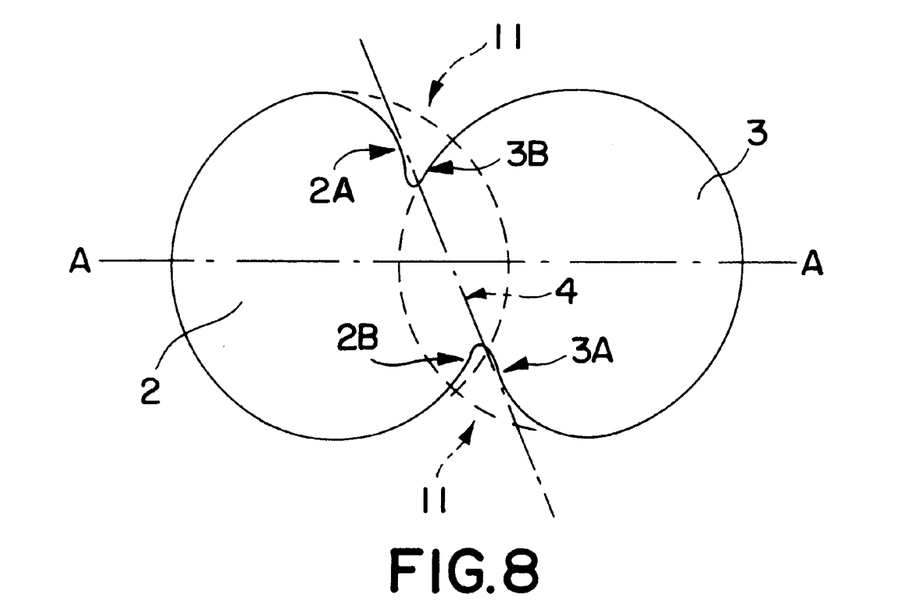
FIG. 8 shows a plan view of a further tablet of this invention.

Referring to FIG. 8 parts in common with FIG. 1 are numbered correspondingly. In FIG. 8 the overall shape of the tablet in plan and section is similar to that shown in FIG. 7, but there is no groove. The two lobes 2, 3 are domed, so that the greatest thickness of the tablet is about the geometric centres of the two lobes 2, 3, with a narrow waist of reduced width and thickness longitudinally between the two lobes 2, 3. The break line 4 is formed by the inherent weakness of the tablet along the line of the waist between the two concave indents 11, aligned diagonally relative to the longitudinal dimension A—A. The concave indents 11 are again asymmetrical about an axis linking their most deeply indented parts, in a manner similar to that shown in FIG. 7.

Figure 9:
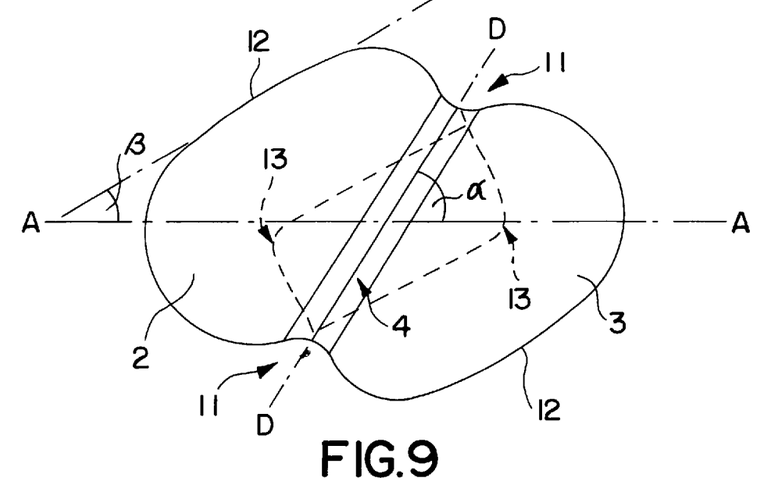
FIG. 9 shows a plan view of a further tablet of this invention.
Figure 10:
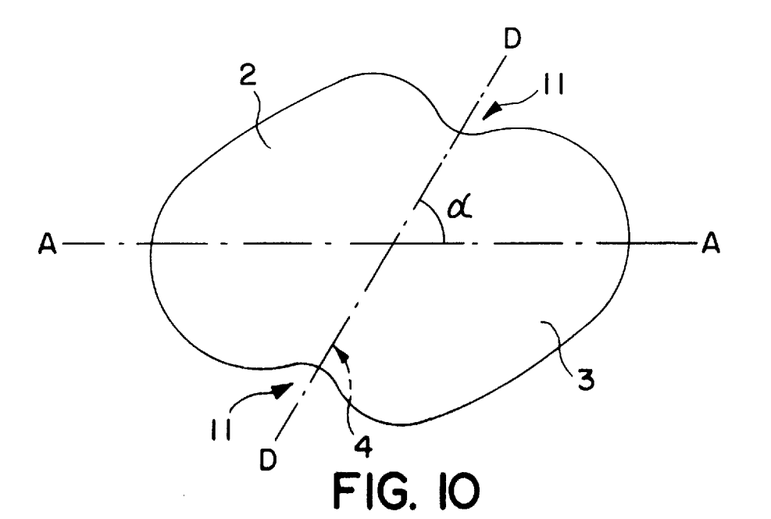
FIG. 10 shows a plan view of a further tablet of this invention.
Figure 11:
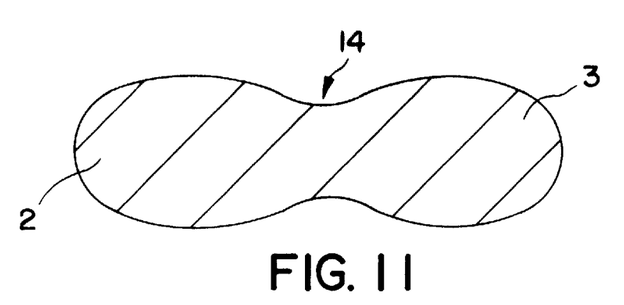
FIG. 11 shows a cross section of the tablet of FIG. 10.

Referring to FIGS. 9, 10 and 11 parts in common with FIG. 1 are numbered correspondingly, but for convenience as the tablets of FIGS. 9 and 10 are of similar shape in plan various features common to FIGS. 9 and 10 are shown in detail in FIG. 9 and omitted in FIG. 10. In FIGS. 9 and 10 the lobes 2, 3 are of generally rectangular shape, with rounded corners and ends. As shown in FIG. 9, the long sides 12 of the rectangular lobes 2, 3 are aligned at an angle b to the longitudinal dimension A—A, and there is a similar alignment in FIG. 10. In FIGS. 9 and 10 the corners shown dotted 13 of the rectangular lobes 2, 3 overlap. In FIGS. 9 and 10 each lobe 2, 3 overlaps the other lobe for ca. 30% of its area as viewed in plan. The area of overlap is itself rectangular, so that the respective long sides of the rectangle overlap for 50% or more, and likewise the respective short sides of the rectangle overlap for 50% or more of their respective length.

About the points where the respective perimeters of the two lobes 2, 3 meet concave indents 11 are formed, which are shaped into a smooth concave indented curve. The lobes 2, 3 are domed so that the thickest parts of the tablets are about the geometric centres of the lobes 2, 3, with a thinned valley or saddle 14 longitudinally in between, following the line of an axis D—D linking the most indented parts of the two indents 11. In FIG. 9 the break line 4 is a "V" sectioned groove extending only across the upper 8 and lower 9 surfaces of the tablet, which are domed. The break line 4 has a bottom which extends in a substantially straight line diagonally across the length dimension A—A, and forming an angle a of about 60° with the length dimension. In FIG. 10 there is no groove, and the break line 4 is formed by the inherent weakness of the tablet along the line of the valley or saddle 14 following the waist between the two concave indents 11.

Figure 12:
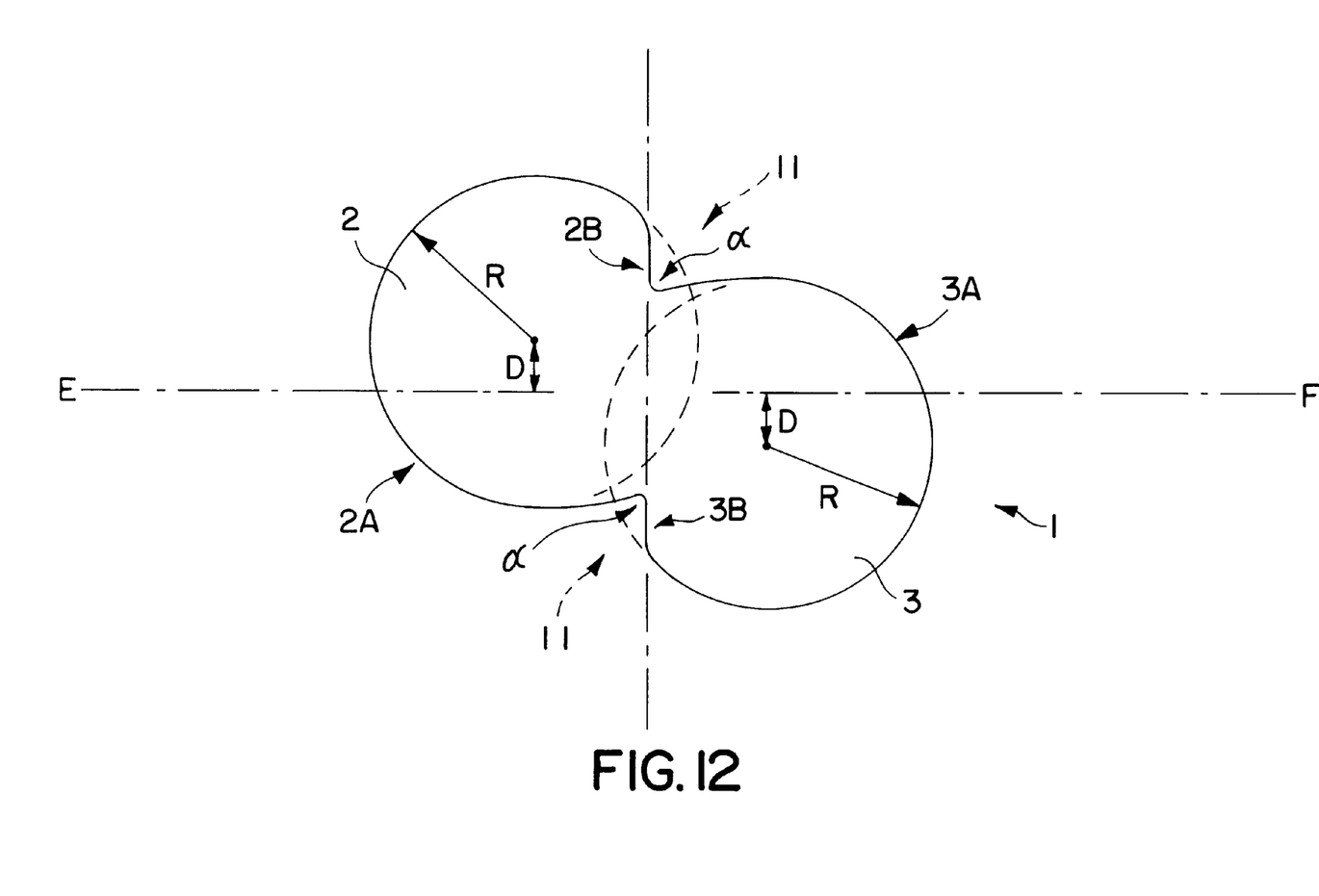
FIG. 12 shows a plan view of a further tablet of this invention.

Referring to FIG. 12, this shows a plan view of a tablet 1 of a shape in which the two lobes 2, 3 are each in plan view of a shape which is substantially circular or oval over 50% or more of their perimeter 2A, 3A, the remainder of the perimeter 2B, 3B of each lobe 2, 3 being a substantially straight line along part of a chord of the said substantially circular or oval part of the perimeter. The two lobes 2, 3 are to some extent semi-circles in shape, or can be described as "D" shaped. The two lobes 2, 3 meet and face each other along the line of the chords 2B, 3B, the chords being aligned transverse to the longitudinal axis of the tablet. The geometric centres of the lobes 2, 3 are respectively displaced relative to each other in a direction parallel to the line of the chords 2B, 3B in respective opposite directions to a distance "D" on either widthways side of the line E--F perpendicular to the line of the chords. The displacement is to the same distance D on respective opposite sides of the said line.

The substantially circular lobes 2, 3 are each of radius R, and the lobes are respectively displaced by ca. 0.3 R relative to each other in a direction parallel to the line of the chords in respective opposite directions on either widthways side of the line E--F.

In the lobes 2, 3 shown in FIG. 12 the perimeter 2A, 3A of each lobe 2, 3 is extended from the projected circular perimeter as shown by the dotted line, to meet the respective chord 3B, 2B of the other lobe, so that the perimeter 2A, 3A meets the chord 3B, 2B at a less acute angle α than a purely circular perimeter 2A, 3A otherwise would. This modifies the shape of the concave indents 11 and consequently the breaking characteristics of the tablet 1 about the line of the chords. The displacement of the centres as shown in FIG. 12 by the distance D means that each lobe bulges 2,3 more prominently widthways to a greater distance or area on one widthways side of the longitudinal axis than the other, and that each lobe 2,3 is differently shaped on one widthways side of the longitudinal axis than the other.

The longitudinal section of the tablet of FIG. 12 is similar to that shown in FIGS. 5 and 11, i.e the two lobes 2, 3 bulge in their thickness dimension with a valley and/or break groove in between the lobes 2, 3.

The tablets 1, 7 are formulated and manufactured in a conventional manner, such that each half 5, 6 contains half the active material content of the tablet plus excipients as common in the art.

The tablets 1, 7 may be broken in the above-described twisting manner, in which the lobes 2, 3 are grasped by the user and are each subjected to respective twisting forces of opposite twist senses about the longitudinal axis A—A. Alternatively the tablets 1, 7 can be broken by a conventional folding snapping action, to split the tablet into two parts substantially about the break line 4. Each part 5, 6 can be taken separately, or alternatively the entire unbroken tablet may be taken whole. The overall rounded shape of the tablet 1, 7 facilitates swallowing.

What is claimed is:

1. A pharmaceutical tablet having a major length dimension and a minor width dimension perpendicular to the length dimension, and having a thickness dimension perpendicular to the length and width dimension, the thickness dimension being less than either the length or width dimension, a break line aligned across a long dimension of the tablet such that a twisting action, in which parts of the tablets on opposite sides of the break line are subjected to rotational twisting force in respectively opposite senses, causes the tablet to break along a line substantially following the break line, into two or more parts, the tablet having upper and lower surfaces which are distanced by the thickness dimension and which are convex and asymmetrical relative to mirror planes parallel to the length or width dimension.

2. A tablet according to claim 1 being of a shape having two lobes which are asymmetrical about a mirror plane aligned parallel to the length dimension.

3. A tablet according to claim 1 being of a shape which bulges in the thickness direction more on one widthways side of the length dimension than on the other.

4. A pharmaceutical tablet having a major length dimension and a minor width dimension perpendicular to the length dimension, and having a thickness dimension perpendicular to the length and width dimension, the thickness dimension being less than either the length or width dimension, a break line aligned across a long dimension of the tablet such that a twisting action, in which parts of the tablets on opposite sides of the break line are subjected to rotational twisting force in respectively opposite senses, causes the tablet to break along a line substantially following the break line, into two or more parts, the tablet being of a shape in which there is an inbuilt twist about the major dimension, such that respective parts of the tablet on longitudinally opposite sides of the break line are each flattened toward a respective plane parallel to the major dimension and to the width of the part, and these respective planes are each rotated about the axis of the major dimension at an angle relative to each other.

5. A tablet according to claim 1, 2, 3 or 4 being of a shape comprising two lobes on either longitudinally disposed side of the longitudinal mid-point of the tablet, with a waist in between which is narrower in width than the widest part of each lobe, longitudinally in between the lobes.

6. A tablet according to claim 5 wherein the shape of each of the two lobes of the tablet is symmetrical about the longitudinal axis.

7. A tablet according to claim 5 wherein the shape of each of the two lobes of the tablet is un-symmetrical about the longitudinal axis.

8. A tablet according to claim 7 wherein each lobe bulges more prominently widthways to a greater distance or area on one widthways side of the longitudinal axis than the other.

9. A tablet according to claim 7 wherein each lobe is differently shaped on one widthways side of the longitudinal axis than the other.

10. A tablet according to claim 7 having upper and lower surfaces distanced by a thickness dimension, and side surfaces between the said upper and lower surfaces, wherein where the side surfaces of the lobes converge toward the narrowed waist of the tablet, the parts of the side surfaces of each lobe on respective opposite sides of the longitudinal axis converge at different angles towards the longitudinal axis.

11. A tablet according to claim 10 wherein the convergence of the side surfaces of each lobe toward the longitudinal axis are steeper on one side of the longitudinal axis than on the other side.

12. A tablet according to claim 5 wherein the tablet is in plan peanut-shaped; dumb-bell shaped; figure of eight-shaped; of a shape with two circular or oval shaped lobes; of a shape with polygonal lobes which may have rounded corners, a corner or edge of each such polygonal lobe overlapping with a corner or edge of the other lobe, of which the circumference, perimeter, edge or corners of each of such lobes overlaps with the circumference, perimeter, edge or corners of the other, or instead of overlapping the circumference, perimeter, edge or corners of the lobes may be longitudinally distanced or may contact tangentially without any overlap.

13. A tablet according to claim 12 wherein the shape in plan comprises two generally circular lobes and in which the extrapolated arcs of the circles meet with no overlap.

14. A tablet according to claim 12 wherein the shape in plan comprises two generally circular lobes of radius R which overlap.

15. A tablet according to claim 14 wherein the overlap is to a distance of about 0.25–0.75 R.

16. A tablet according to claim 12 wherein the lobes are generally oval and their extrapolated arcs meet with no overlap.

17. A tablet according to claim 12 wherein the lobes are generally oval and their extrapolated arcs overlap.

18. A tablet according to claim 9 wherein on either widthways side of such two-lobed tablets a concave indent exists, and the waist of the tablet extends between these indents, the concave indent being asymmetrical about an axis linking the most deeply indented parts of the indents.

19. A tablet according to claim 18 wherein part of the perimeter of the lobe immediately adjacent to the indent is aligned more steeply toward the longitudinal axis than the corresponding part of the perimeter on the longitudinally opposite side of the indent.

20. A tablet according to claim 13 wherein the respective geometric centres of each of the lobes, is displaced to respective opposite sides of the long dimension, in the plane in which the tablet shape is flattened.

21. A tablet according to claim 20 wherein the lobes are generally circular or generally oval lobes and the centres are displaced to 0.05–0.3 of radius R on each side of the long dimension.

22. A tablet according to claim 12 wherein the shape of the tablet in plan comprises two generally quadrilateral shaped lobes and an extrapolated corner or side of each such lobe overlaps with a corner or side of the other lobe.

23. A tablet according to claim 22 wherein the overlap is up to ca. 50% of the respective areas of the lobes as viewed perpendicular to the plane in which they are flattened.

24. A tablet according to claim 12 wherein the perimeters of the lobes are longitudinally distanced or contact tangentially without any overlap.

25. A tablet according to claim 22 wherein the lobes are generally rectangular lobes and overlap and the area of overlap is itself rectangular.

26. A tablet according to claim 22 wherein the shape of each of the two generally quadrilateral lobes of the tablet is un-symmetrical about the longitudinal axis.

27. A tablet according to claim 12 wherein the two lobes are each in plan view of a shape which is substantially circular or oval over 50% or more of their perimeter, the remainder of the perimeter of each lobe being a substantially straight line the line of a chord or part of a chord of the said substantially circular or oval part of the perimeter, the two lobes meeting and facing each other along the line of the chords, the chords being aligned transverse to the longitudinal axis of the tablet, the geometric centres of the lobes being respectively displaced relative to each other in a direction parallel to the line of the chords in respective opposite directions on either widthways side of a line perpendicular to the line of the chords.

28. A tablet according to claim 27 wherein the lobes are substantially circular lobes of radius R and the lobes are respectively displaced by 0.1–0.8 R relative to each other in a direction parallel to the line of the chords in respective opposite directions on either widthways side of a line perpendicular to the line of the chords.

29. A tablet according to claim 2, 3, or 4 characterised in that the break line crosses the major dimension at an angle other than 90°.

30. A tablet according to claim 1, 2, 3, or 4 characterised in that the break line runs between concave indents on widthways opposite sides of the tablet.

* * * * *